(12) United States Patent
Wirbisky et al.

(10) Patent No.: US 9,539,433 B1
(45) Date of Patent: Jan. 10, 2017

(54) ELECTRODE IMPLANTATION IN A PELVIC FLOOR MUSCULAR STRUCTURE

(75) Inventors: Alan G. Wirbisky, Brooklyn Park, MN (US); Andrew P. VanDeWeghe, St. Louis Park, MN (US); Peter Rehder, Innsbruck (AT)

(73) Assignee: Astora Women's Health, LLC, Eden Prairie, MN (US)

( * ) Notice: Subject to any disclaimer, the term of this patent is extended or adjusted under 35 U.S.C. 154(b) by 2260 days.

(21) Appl. No.: 12/406,434

(22) Filed: Mar. 18, 2009

(51) Int. Cl.
*A61N 1/00* (2006.01)
*A61N 1/38* (2006.01)

(52) U.S. Cl.
CPC ........................ *A61N 1/38* (2013.01)

(58) Field of Classification Search
CPC ................................ A61N 1/36; A61N 1/32
USPC ....................... 607/41, 40, 39, 116
See application file for complete search history.

(56) References Cited

U.S. PATENT DOCUMENTS

| | | | |
|---|---|---|---|
| 3,628,538 A | 12/1971 | Vincent et al. | 128/422 |
| 3,640,284 A | 2/1972 | De Langis | |
| 3,646,940 A | 3/1972 | Timm et al. | |
| 3,650,276 A | 3/1972 | Burghele et al. | |
| 3,662,758 A | 5/1972 | Glover | 128/419 |
| 3,667,477 A | 6/1972 | Susset et al. | |
| 3,866,613 A | 2/1975 | Kenny et al. | |
| 3,870,051 A | 3/1975 | Brindley | |
| 3,926,178 A | 12/1975 | Feldzamen | |
| 3,941,136 A | 3/1976 | Bucalo | |
| 3,983,865 A | 10/1976 | Shepard | |
| 3,983,881 A | 10/1976 | Wickham | |
| 4,010,758 A | 3/1977 | Rockland et al. | |
| 4,023,574 A | 5/1977 | Nemec | |
| 4,030,509 A | 6/1977 | Heilman et al. | |
| 4,044,774 A | 8/1977 | Corbin et al. | 128/404 |
| 4,106,511 A | 8/1978 | Erlandsson | |

(Continued)

FOREIGN PATENT DOCUMENTS

| | | |
|---|---|---|
| DE | 8506522.6 U1 | 6/1985 |
| EP | 0245547 | 5/1986 |

(Continued)

OTHER PUBLICATIONS http://www.obgyn.net/cpp/images/voiding_image2.gif.*

(Continued)

*Primary Examiner* — Christopher D Koharski
*Assistant Examiner* — Nadia A Mahmood
(74) *Attorney, Agent, or Firm* — Westman, Champlin & Koehler, P.A.; Brian D. Kaul

(57) ABSTRACT

In a method of implanting an electrode of an electronic stimulator device into a pelvic floor muscular structure of a patient, a stimulation lead having a proximal end and a distal end comprising an electrode is provided. The distal end of the stimulation lead is fed along a path, which is adjacent the pubic symphysis of a patient, toward a pelvic floor muscular structure of the patient. The distal end of the stimulation lead is then fed into the pelvic floor muscular structure of the patient. In one embodiment, the pelvic floor muscular structure comprises the external urinary sphincter of the patient. In accordance with other embodiments, the pelvic floor muscular structure comprises one of the external anal sphincter, the levator ani muscle, the puborectalis sling muscle and prostate tissue.

20 Claims, 9 Drawing Sheets

(56) References Cited

U.S. PATENT DOCUMENTS

| | | | |
|---|---|---|---|
| 4,136,684 A | 1/1979 | Scattergood et al. | |
| 4,139,006 A | 2/1979 | Corey | |
| 4,153,059 A | 5/1979 | Fravel et al. | |
| 4,157,087 A | 6/1979 | Miller et al. | |
| 4,165,750 A | 8/1979 | Aleev et al. | |
| 4,177,819 A | 12/1979 | Kofsky et al. | |
| 4,222,377 A | 9/1980 | Burton | |
| 4,290,420 A | 9/1981 | Manetta | |
| 4,387,719 A | 6/1983 | Plevnik et al. | |
| 4,402,328 A | 9/1983 | Doring | |
| 4,406,288 A | 9/1983 | Horwinski et al. | |
| 4,414,986 A | 11/1983 | Dickhudt et al. | |
| 4,431,001 A | 2/1984 | Hakansson et al. | |
| 4,457,299 A | 7/1984 | Cornwell | |
| 4,492,233 A | 1/1985 | Petrofsky et al. | |
| 4,515,167 A | 5/1985 | Hochman | |
| 4,542,753 A | 9/1985 | Brenman et al. | |
| 4,568,339 A | 2/1986 | Steer | |
| 4,569,351 A | 2/1986 | Tang | |
| 4,571,749 A | 2/1986 | Fischell | |
| 4,580,578 A | 4/1986 | Barsom | |
| 4,585,005 A | 4/1986 | Lue et al. | |
| 4,602,624 A | 7/1986 | Naples et al. | |
| 4,607,639 A | 8/1986 | Tanagho et al. | |
| 4,628,942 A | 12/1986 | Sweeney et al. | |
| 4,688,575 A | 8/1987 | DuVall | |
| 4,703,755 A | 11/1987 | Tanagho et al. | |
| 4,731,083 A | 3/1988 | Fischell | |
| 4,735,205 A | 4/1988 | Chachques et al. | |
| 4,739,764 A | 4/1988 | Lue et al. | |
| 4,750,494 A | 6/1988 | King | |
| 4,771,779 A | 9/1988 | Tanagho et al. | |
| 4,785,828 A | 11/1988 | Maurer | |
| 4,881,526 A | 11/1989 | Johnson et al. | |
| 4,913,164 A | 4/1990 | Greene et al. | |
| 4,941,874 A | 7/1990 | Sandow et al. | |
| 5,013,292 A | 5/1991 | Lemay | |
| 5,019,032 A | 5/1991 | Robertson | |
| 5,082,006 A | 1/1992 | Jonasson | |
| 5,094,242 A | 3/1992 | Gleason et al. | |
| 5,103,835 A | 4/1992 | Yamada et al. | 128/734 |
| 5,112,344 A | 5/1992 | Petros | |
| 5,193,539 A | 3/1993 | Schulman et al. | |
| 5,193,540 A | 3/1993 | Schulman et al. | |
| 5,199,430 A | 4/1993 | Fang et al. | |
| 5,285,781 A | 2/1994 | Brodard | |
| 5,291,902 A | 3/1994 | Carman | |
| 5,312,439 A | 5/1994 | Loeb | |
| 5,324,316 A | 6/1994 | Schulman et al. | |
| 5,324,323 A | 6/1994 | Bui | |
| 5,324,324 A | 6/1994 | Vachon et al. | |
| 5,330,507 A | 7/1994 | Schwartz | |
| 5,358,514 A | 10/1994 | Schulman et al. | |
| 5,366,493 A | 11/1994 | Scheiner et al. | |
| 5,370,670 A | 12/1994 | Chancellor | |
| 5,385,577 A | 1/1995 | Maurer et al. | |
| 5,405,367 A | 4/1995 | Schulman et al. | |
| 5,411,548 A | 5/1995 | Carman | 607/138 |
| 5,417,226 A | 5/1995 | Juma | |
| 5,423,329 A | 6/1995 | Ergas | |
| 5,425,751 A | 6/1995 | Baeten et al. | |
| 5,452,719 A | 9/1995 | Eisman et al. | |
| 5,484,445 A | 1/1996 | Knuth | |
| 5,518,504 A | 5/1996 | Polyak | |
| 5,520,606 A | 5/1996 | Schoolman et al. | 600/31 |
| 5,562,717 A | 10/1996 | Tippey et al. | 607/41 |
| 5,569,351 A | 10/1996 | Menta et al. | |
| 5,571,148 A | 11/1996 | Loeb et al. | |
| 5,611,515 A | 3/1997 | Benderev et al. | |
| 5,611,768 A | 3/1997 | Tutrone, Jr. | |
| 5,634,462 A | 6/1997 | Tyler et al. | |
| 5,702,428 A | 12/1997 | Tippey et al. | |
| 5,752,978 A | 5/1998 | Chancellor | |
| 5,766,229 A | 6/1998 | Bornzin | |
| 5,785,666 A | 7/1998 | Costello et al. | |
| 5,807,397 A | 9/1998 | Barreras | 607/61 |
| 5,824,027 A | 10/1998 | Hoffer et al. | |
| 5,833,595 A | 11/1998 | Lin | |
| 5,836,994 A | 11/1998 | Bourgeois | |
| 5,842,478 A | 12/1998 | Benderev et al. | |
| 5,860,425 A | 1/1999 | Benderev et al. | |
| 5,876,353 A | 3/1999 | Riff | |
| 5,899,909 A | 5/1999 | Claren et al. | |
| 5,927,282 A | 7/1999 | Lenker et al. | |
| 5,941,903 A | 8/1999 | Zhu et al. | |
| 5,954,761 A | 9/1999 | Machek et al. | |
| 5,957,920 A | 9/1999 | Baker | |
| 5,957,965 A | 9/1999 | Moumane et al. | |
| 5,963,097 A | 10/1999 | Garachtchenko et al. | |
| 5,978,712 A | 11/1999 | Suda et al. | 607/41 |
| 5,984,854 A | 11/1999 | Ishikawa et al. | |
| 6,002,964 A | 12/1999 | Feler et al. | |
| 6,026,326 A | 2/2000 | Bardy | |
| 6,027,456 A | 2/2000 | Feler et al. | |
| 6,038,463 A | 3/2000 | Laske et al. | |
| 6,039,686 A | 3/2000 | Kovac | |
| 6,042,534 A | 3/2000 | Gellman et al. | |
| 6,051,017 A | 4/2000 | Loeb et al. | |
| 6,055,456 A | 4/2000 | Gerber | |
| 6,061,596 A | 5/2000 | Richmond et al. | 607/41 |
| 6,078,840 A | 6/2000 | Stokes | |
| 6,104,955 A | 8/2000 | Bourgeois | |
| 6,104,960 A | 8/2000 | Duysens et al. | |
| 6,110,101 A | 8/2000 | Tihon et al. | |
| 6,128,536 A | 10/2000 | Noack et al. | |
| 6,131,575 A | 10/2000 | Lenker et al. | |
| 6,135,945 A | 10/2000 | Sultan | |
| 6,161,029 A | 12/2000 | Spreigl et al. | |
| 6,178,356 B1 | 1/2001 | Chastain et al. | |
| 6,185,452 B1 | 2/2001 | Schulman et al. | |
| 6,208,894 B1 | 3/2001 | Schulman et al. | |
| 6,238,423 B1 | 5/2001 | Bardy | |
| 6,240,315 B1 | 5/2001 | Mo et al. | |
| 6,240,316 B1 | 5/2001 | Richmond et al. | |
| 6,243,607 B1 | 6/2001 | Mintchev et al. | |
| 6,266,557 B1 | 7/2001 | Roe et al. | |
| 6,266,564 B1 | 7/2001 | Hill et al. | |
| 6,328,686 B1 | 12/2001 | Kovac | 600/30 |
| 6,341,236 B1 | 1/2002 | Osorio et al. | |
| 6,354,991 B1 | 3/2002 | Gross et al. | 600/29 |
| 6,360,750 B1 | 3/2002 | Gerber et al. | |
| 6,366,814 B1 | 4/2002 | Boveja et al. | |
| 6,382,214 B1 | 5/2002 | Raz et al. | |
| 6,397,109 B1 | 5/2002 | Cammilli et al. | |
| 6,407,308 B1 | 6/2002 | Roe et al. | |
| 6,418,930 B1 | 7/2002 | Fowler | |
| 6,582,441 B1 | 6/2003 | He et al. | |
| 6,600,956 B2 | 7/2003 | Maschino et al. | |
| 6,612,977 B2 | 9/2003 | Staskin et al. | |
| 6,641,524 B2 | 11/2003 | Kovac | |
| 6,650,943 B1 | 11/2003 | Whitehurst et al. | |
| 6,652,449 B1 | 11/2003 | Gross et al. | |
| 6,652,450 B2 | 11/2003 | Neisz et al. | |
| 6,652,499 B1 | 11/2003 | Edgren et al. | |
| 6,658,297 B2 | 12/2003 | Loeb | |
| 6,659,936 B1 | 12/2003 | Furness et al. | |
| 6,712,772 B2 | 3/2004 | Cohen et al. | |
| 6,735,474 B1 | 5/2004 | Loeb et al. | |
| 6,802,807 B2 | 10/2004 | Anderson et al. | |
| 6,836,684 B1 | 12/2004 | Rijkhoff et al. | |
| 6,862,480 B2 | 3/2005 | Cohen et al. | 600/30 |
| 6,896,651 B2 | 5/2005 | Gross et al. | |
| 6,911,003 B2 | 6/2005 | Anderson et al. | |
| 6,941,171 B2 | 9/2005 | Mann et al. | |
| 6,952,613 B2 | 10/2005 | Swoyer et al. | |
| 6,964,643 B2 | 11/2005 | Hovland et al. | |
| 6,964,699 B1 | 11/2005 | Carns et al. | |
| 6,971,393 B1 | 12/2005 | Mamo et al. | |
| 7,054,689 B1 | 5/2006 | Whitehurst et al. | |
| 7,079,882 B1 | 7/2006 | Schmidt | |
| 7,120,499 B2 | 10/2006 | Thrope et al. | 607/48 |
| 7,319,905 B1 | 1/2008 | Morgan et al. | |
| 7,328,068 B2 | 2/2008 | Spinelli et al. | 607/39 |
| 7,330,764 B2 | 2/2008 | Swoyer et al. | |

(56) References Cited

U.S. PATENT DOCUMENTS

| | | |
|---|---|---|
| 7,343,202 B2 | 3/2008 | Mrva et al. ............. 607/41 |
| 7,376,467 B2 | 5/2008 | Thrope et al. ............. 607/48 |
| 7,387,603 B2 | 6/2008 | Gross et al. |
| 7,582,053 B2 | 9/2009 | Gross et al. |
| 7,613,516 B2 | 11/2009 | Cohen et al. |
| 7,628,795 B2 | 12/2009 | Karwoski et al. |
| 7,647,113 B2 | 1/2010 | Wirbisky et al. |
| 7,771,345 B1 | 8/2010 | O'Donnell |
| 7,890,176 B2 | 2/2011 | Jaax et al. |
| 8,083,663 B2 | 12/2011 | Gross et al. |
| 2001/0002441 A1 | 5/2001 | Boveja |
| 2001/0003799 A1 | 6/2001 | Boveja |
| 2001/0018549 A1 | 8/2001 | Scetbon |
| 2002/0055761 A1 | 5/2002 | Mann et al. |
| 2002/0099259 A1 | 7/2002 | Anderson et al. |
| 2002/0161382 A1 | 10/2002 | Neisz et al. |
| 2002/0165566 A1 | 11/2002 | Ulmsten |
| 2003/0018365 A1 | 1/2003 | Loeb |
| 2003/0023296 A1 | 1/2003 | Osypka |
| 2003/0028232 A1 | 2/2003 | Camps et al. |
| 2003/0100930 A1 | 5/2003 | Cohen et al. |
| 2003/0171644 A1 | 9/2003 | Anderson et al. |
| 2003/0199961 A1 | 10/2003 | Bjorklund et al. |
| 2003/0212305 A1 | 11/2003 | Anderson et al. |
| 2003/0236557 A1 | 12/2003 | Whitehurst et al. |
| 2003/0236558 A1 | 12/2003 | Whitehurst et al. |
| 2004/0015057 A1 | 1/2004 | Rocheleau et al. |
| 2004/0015204 A1 | 1/2004 | Whitehurst et al. |
| 2004/0015205 A1 | 1/2004 | Whitehurst et al. |
| 2004/0039453 A1 | 2/2004 | Anderson et al. |
| 2004/0059392 A1 | 3/2004 | Parramon et al. |
| 2004/0068203 A1 | 4/2004 | Gellman et al. |
| 2004/0093053 A1 | 5/2004 | Gerber et al. |
| 2004/0242956 A1 | 12/2004 | Scorvo |
| 2004/0248979 A1 | 12/2004 | Brettman et al. |
| 2005/0038489 A1 | 2/2005 | Grill |
| 2005/0043580 A1 | 2/2005 | Watschke et al. |
| 2005/0049648 A1 | 3/2005 | Cohen et al. |
| 2005/0065395 A1 | 3/2005 | Mellier |
| 2005/0113877 A1 | 5/2005 | Spinelli et al. |
| 2005/0119710 A1 | 6/2005 | Furness et al. |
| 2005/0143618 A1 | 6/2005 | Anderson et al. |
| 2005/0149156 A1 | 7/2005 | Libbus et al. |
| 2005/0216069 A1 | 9/2005 | Cohen et al. |
| 2005/0228346 A1 | 10/2005 | Goode et al. |
| 2005/0245787 A1 | 11/2005 | Cox et al. |
| 2005/0245874 A1 | 11/2005 | Carrez et al. |
| 2005/0250977 A1 | 11/2005 | Montpetit et al. |
| 2005/0283235 A1 | 12/2005 | Kugler et al. |
| 2006/0004421 A1 | 1/2006 | Bennett et al. ............. 607/41 |
| 2006/0004429 A1* | 1/2006 | Mrva et al. ............. 607/116 |
| 2006/0149345 A1 | 7/2006 | Boggs, II et al. |
| 2006/0241733 A1 | 10/2006 | Zhang et al. |
| 2006/0287571 A1 | 12/2006 | Gozzi et al. ............. 600/30 |
| 2007/0021650 A1 | 1/2007 | Rocheleau et al. |
| 2007/0043416 A1 | 2/2007 | Callas et al. |
| 2007/0123952 A1 | 5/2007 | Strother et al. ............. 607/48 |
| 2007/0179559 A1 | 8/2007 | Giftakis et al. |
| 2007/0185541 A1 | 8/2007 | DiUbaldi et al. |
| 2007/0239224 A1 | 10/2007 | Bennett et al. ............. 607/41 |
| 2007/0253998 A1 | 11/2007 | Giftakis et al. |
| 2007/0255333 A1 | 11/2007 | Giftakis et al. |
| 2007/0260288 A1 | 11/2007 | Gross et al. |
| 2008/0009914 A1 | 1/2008 | Buysman et al. |
| 2008/0071321 A1 | 3/2008 | Boggs, II et al. ............. 607/39 |
| 2008/0132969 A1 | 6/2008 | Bennett et al. ............. 607/41 |
| 2008/0242918 A1 | 10/2008 | Gross et al. |
| 2009/0012592 A1 | 1/2009 | Buysman et al. |
| 2009/0036946 A1 | 2/2009 | Cohen et al. |
| 2009/0043356 A1 | 2/2009 | Longhini et al. |
| 2009/0157091 A1 | 6/2009 | Buysman |
| 2010/0049289 A1 | 2/2010 | Lund et al. |
| 2010/0076254 A1 | 3/2010 | Jimenez et al. |

FOREIGN PATENT DOCUMENTS

| | | |
|---|---|---|
| EP | 1 119 314 | 10/1999 |
| EP | 1 661 600 A1 | 5/2006 |
| GB | 2309388 | 7/1997 |
| WO | 9012617 | 11/1990 |
| WO | 9604955 | 2/1996 |
| WO | 9632916 | 10/1996 |
| WO | 9817190 A2 | 4/1998 |
| WO | 0000082 A1 | 1/2000 |
| WO | 0001320 | 1/2000 |
| WO | WO 00/19940 | 4/2000 |
| WO | 0239890 A2 | 5/2002 |
| WO | 02069781 | 9/2002 |
| WO | 02078592 | 10/2002 |
| WO | 03002192 | 1/2003 |
| WO | 2005122954 A1 | 12/2005 |
| WO | 2006047833 | 5/2006 |
| WO | 2007097994 A2 | 8/2007 |
| WO | WO 2007/126632 | 11/2007 |
| WO | 2007145913 A1 | 12/2007 |
| WO | 2010107751 A2 | 9/2010 |

OTHER PUBLICATIONS

European Search Report and Written Opinion of 06011641.5 completed Aug. 21, 2006.
International Search Report and Written Opinion of PCT/US2007/004474 filed Feb. 22, 2007.
U.S. Appl. No. 60/779,219, filed Mar. 3, 2006.
U.S. Appl. No. 12/558,143, filed Sep. 11, 2009.
International Search Report and Written Opinion of PCT/US2007/000112 filed Jan. 3, 2007.
U.S. Appl. No. 61/160,765, filed Mar. 17, 2009.
Dietz et al., Mechanical Properties of Urogynecologic Implant Materials, Int. Urogynecol J. (2003) 14:239-243.
Iglesia et al., "The Use of Mesh in Gynecologic Surgery", Int. Urogynecol J. (1997) 8:105-115.
Partial European Search Report from European Patent Application No. 10176162.5, mailed Jan. 21, 2011.
Yamamoto et al., "Optimal parameters for effective electrical stimulation of the anal sphincters in a child with fecal incontinence: preliminary report," Pediatr Surg Int (1993) 8:132-137.
Yamanishi et al., "Electrical Stimulation for Stress Incontinence", Int. Urogynecol J (1998) 9:281-290 Springer-Verlag London Ltd.
Caldwell, K.P.S. "The Use of Electrical Stimulation in Urinary Retention and Incontinence [Abridged]." Section of Urology, vol. 61, pp. 35-39, Jul. 1968.
Caldwell, K.P.S. et al. "Urethral Pressure Recordings in Male Incontinents Under Electrical Stimulation." Investigative Urology vol. 5, No. 6, pp. 572-579, May 1968.
Caldwell, K.P.S. et al. "Stress Incontinence in Females: Report on 31 Cases Treated by Electrical Implant." J. Obstet. Gynaec. Brit. Cwlth vol. 75, pp. 777-780, Jul. 1968.
Caldwell, K.P.S. "Electrical Stimulation.", Sphincter Research Unit, Royal Devon and Exeter Hospital, Exeter (England), Urol. Int. 29: 225, 1974.(1 page).
U.S. Appl. No. 60/578,742, filed Jun. 10, 2004.
Extended European Search Report from European Patent Application No. 10176162.5, mailed Apr. 28, 2011.
International Search Report and Written Opinion from PCT/US2011/023677 dated Apr. 21, 2011.
U.S. Appl. No. 11/746,476, filed May 9, 2007.
A first Communication issued by the European Patent Office for European Patent Application No. 07795734.8, dated Nov. 17, 2010.
Notification of a First Office Action from Chinese Patent Application No. 200780021028.1, issued Jun. 1, 2010.
International Preliminary Report on Patentability and Written Opinion of PCT/US2007/013190, filed Jun. 5, 2007.
Merrill Daniel C. et al., "Treatment with Electrical Stimulation of the Pelvic Floor", Urology, Jan. 1975, vol. V, No. 1, pp. 67-72.
Chai et al., "Percutaneous Sacral Third Nerve Root Neurostimulation Improves Symptoms and Normalizes Urinary HB-EGF Levels

(56) References Cited

OTHER PUBLICATIONS and Antiproliferative Activity in Patients with Interstitial Cystitis", Urology, 55(5), pp. 643-646, May 2000.

Fall et al., "Electrical Stimulation in Interstitial Cystitis", Journal of Urology, 123(2), pp. 192-195, Feb. 1980.

Zermann et al., "Sacral Nerve Stimulation for Pain Relief in Interstitial Cystitis", Urol. Int., 65(2), pp. 120-121, 2000.

Caraballo et al., "Sacral Nerve Stimulation as a Treatment for Urge Incontinence and Associated Pelvic Floor Disorders at a Pelvic Floor Center: A Follow-up Study", Urology, 57(6 Suppl 1), p. 121, Jun. 2001.

P.D., O'Donnell ed., Urinary Incontinence, Chap. 26, 1997, Mosby Publishers, St. Louis, MI pp. 197-2002.

Medtronic®'s "InterStim Therapy for Urinary Control-Patient Stories", 1997, Medtronic, Inc., Spring Lake Park, MN 2 pages.(http://webprod1.medtronic.com/neuro/interstim/4Bsize.html).

Summary of Safety and Effectiveness of Medtronic® InterStim® Sacral Nerve Stimulation(SNS)TM System, Sep. 1997, Medtronic, Inc., Spring Lake Park, MN, 2 pages.

Medtronic®'s "InterStim Therapy for Urinary . . . for People with Bladder Control Problem", 1997, Medtronic, Inc., Spring Lake Park, MN, 2 pages. (http://webprod1.medtronic.com/neuro/interstim/1types.html).

A supplementary European Search Report for European Patent Application No. 02793278.9, dated Feb. 14, 2011.

U.S. Appl. No. 60/805,036, filed Jun. 16, 2006.

U.S. Appl. No. 60/803,954, filed Jun. 5, 2006.

\* cited by examiner

ELECTRODE IMPLANTATION IN A PELVIC FLOOR MUSCULAR STRUCTURE

FIELD OF THE INVENTION

Embodiments of the present invention generally relate to the implantation of an electrode into a pelvic floor muscular structure of a patient.

BACKGROUND

Implantable electronic stimulator devices, such as neuromuscular stimulation devices, have been disclosed for use in the treatment of various pelvic conditions, such as urinary incontinence, fecal incontinence and sexual dysfunction. Such devices generally include one or more electrodes that are coupled to a control unit by leads. Electrical signals are applied to the desired pelvic muscle of the patient through electrodes in order to treat the condition. Exemplary implantable electronic stimulator devices and uses of the devices are disclosed in U.S. Pat. Nos. 6,354,991, 6,652,449, 6,712,772 and 6,862,480, each of which is hereby incorporated by reference in its entirety.

SUMMARY

Embodiments of the present invention are generally directed to a method of implanting an electrode of an electronic stimulator device into a pelvic floor muscular structure of a male or female patient. In one embodiment of the method, a stimulation lead having a proximal end and a distal end comprising an electrode is provided. The distal end of the stimulation lead is fed along a path, which is adjacent the pubic symphysis of a patient, toward a pelvic floor muscular structure of the patient. The distal end of the stimulation lead is then fed into the pelvic floor muscular structure of the patient. In one embodiment, the pelvic floor muscular structure comprises the external urinary sphincter of the patient. In accordance with other embodiments, the pelvic floor muscular structure comprises one of the external anal sphincter, the levator ani muscle, the puborectalis sling muscle and prostate tissue.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Embodiments of the present invention are directed to a method of implanting an electrode of an electronic stimulator device into a pelvic floor muscular structure of a male or female patient. In one embodiment, the patient is a male patient. Before discussing various embodiments of the method of implanting the electrode, exemplary implantable electronic stimulator devices will be described with reference to FIGS. 1 and 2.

Figure 1:
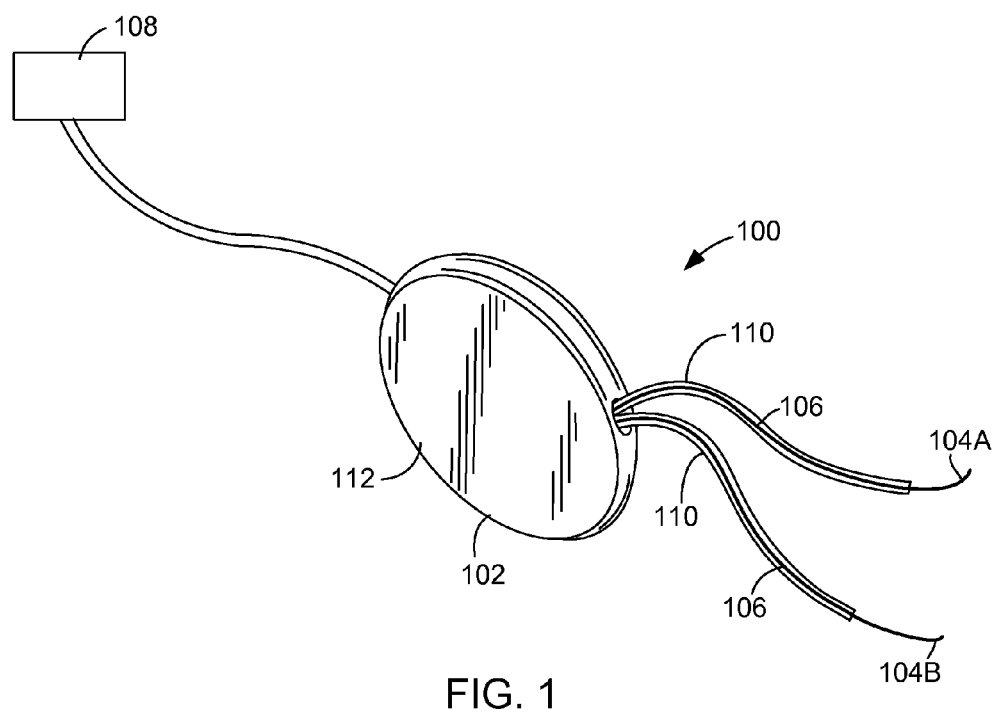
FIG. 1 is a schematic, pictorial view of an exemplary implantable electronic stimulator device in accordance with embodiments of the invention.

FIG. 1 is a schematic, pictorial view of an exemplary implantable electronic stimulator device 100, in accordance with embodiments of the invention. Device 100 is configured for implantation into the pelvic region of a patient, as described in detail below. The device 100 can be used to provide muscle and/or nerve stimulation to control and/or treat a pelvic condition, such as pelvic pain, urinary incontinence and other pelvic conditions. In one embodiment, the device 100 comprises a control unit 102 and one or more electrodes, generally referred to as 104, such as electrodes 104A and 104B. Electrodes 104 are coupled to the control unit 102 by leads 106. In one embodiment, the device 100 includes at least one physiological sensor 108, such as a miniature ultrasound transducer, one or more accelerometers, a pressure transducer or other sensors known in the art.

In one embodiment, the control unit 102 comprises circuitry for senses electrical signals received by the electrodes 104, such as electromyogram (EMG) signals, along with circuitry for processing the signals from the sensor 108. In one embodiment, the control unit 104 comprises circuitry for applying electrical stimulation waveforms (i.e., electrical signals) to one or more of the electrodes 104. The electrical stimulation waveforms are designed to control and/or treat the desired condition of the pelvic region.

In one embodiment, the control unit 102 and the electrodes 104 are as described in the above-referenced patents, in PCT Patent Publication WO 00-19940, entitled "Incontinence Treatment Device," and/or in PCT Patent Publication WO 00-19939, entitled "Control of Urge Incontinence," with appropriate changes as are otherwise indicated by clinical and engineering considerations that are clear to those skilled in the art.

In one embodiment, the electrodes 104 are flexible intramuscular-type wire electrodes, approximately 1-35 millimeters long and 50-100 microns in diameter, in order to minimize patient discomfort. In one embodiment, the electrodes 104 comprise a spiral hook, as known in the art, so that they can be easily and permanently anchored in a pelvic muscle of a patient. The wire, from which the electrodes 104 are made, comprises a suitable conductive material, such as a biocompatible metal such as silver, a platinum/iridium alloy (90-10) or a nickel-chromium alloy. The leads 106 have a length that is suitable for the application, such as 5-10 centimeters long, and are surrounded by an insolating jacket 110 typically comprising silicone, polyurethane or and other flexible, biocompatible insolating material. An optional additional wire (not shown) inside the jacket 110 can serve as an antenna for the purpose of wireless communications with the device 100, in accordance with known methods.

In one embodiment, the control unit 102 comprises a circuitry for processing electrical signals received from the electrodes 104 and/or for applying an electrical waveform to one or both of the electrodes 104. In one embodiment, the circuitry is contained in a case 112 made of titanium or other suitable biocompatible metal. Typically, the case 112 is about 20 millimeters in diameter and 4 millimeters thick. For some applications, the case 112 serves as a ground electrode for the electrodes 104 when they are sensing or stimulating in a monopolar mode. Alternatively, the case 112 may comprise metal coated with a layer of biocompatible plastic, such as polymethyl methacrylate (PMMA) or silicon.

Figure 2:
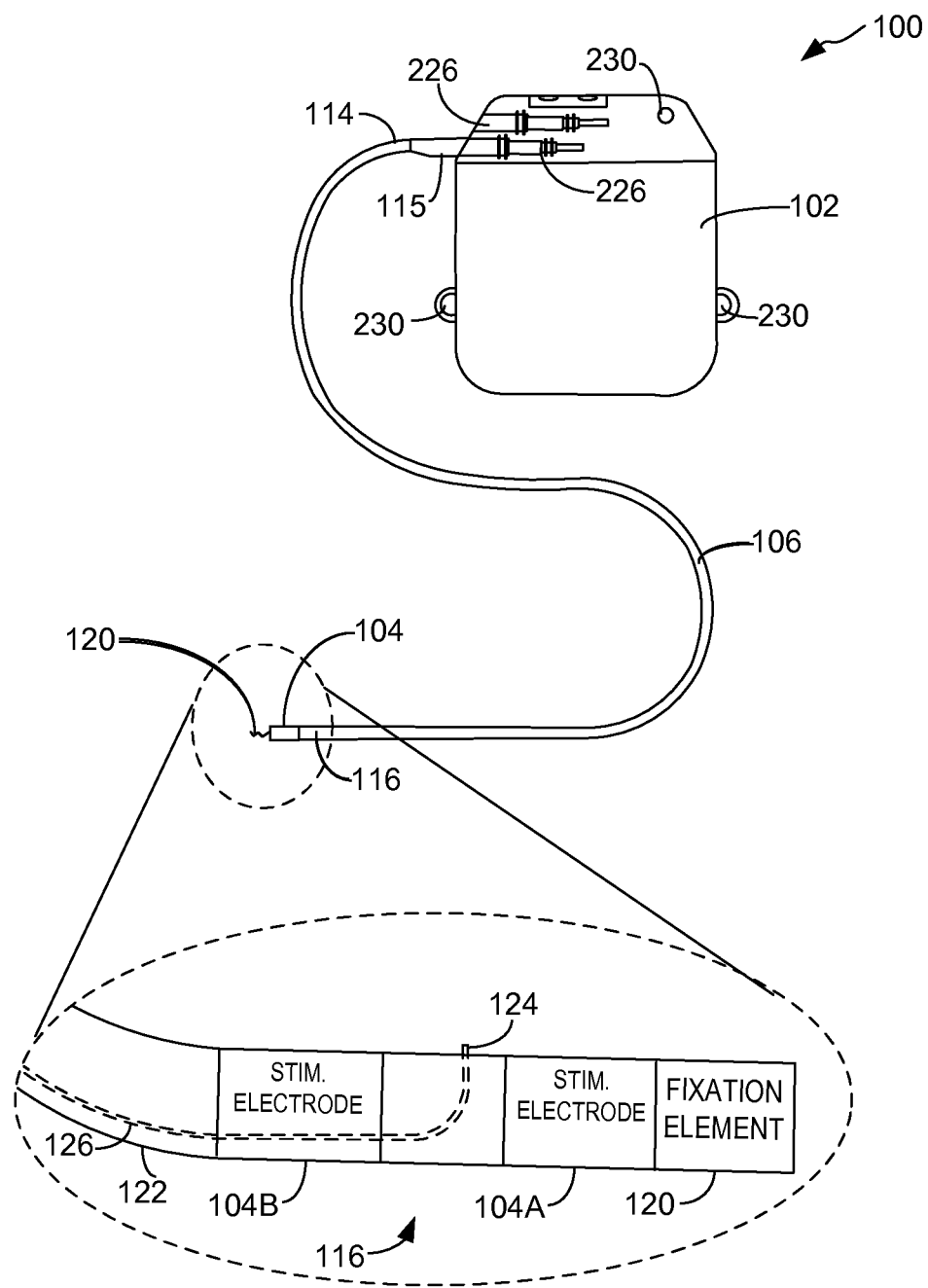
FIG. 2 is a side plan view of an exemplary electronic stimulator device, in accordance with embodiments of the invention.

Although two electrodes 104A and 104B and one sensor 108 are shown attached to the control unit 102 in FIG. 1, it is possible to use only a single electrode 104, as illustrated in FIG. 2, which is a side plan view of an exemplary electronic stimulator device 100, in accordance with another embodiment of the invention. Except with respect to the difference described below, the embodiment of the device 100 shown in FIG. 2 is generally similar to the embodiments shown in FIG. 1, and techniques described herein with respect to one of these configurations can generally be applied to the other configuration. Accordingly, elements in FIG. 2 that are labeled with the same or similar numbers as that used in FIG. 1, generally correspond to the same or similar elements.

One embodiment of the device 100 shown in FIG. 2 comprises a control unit 102, at least one electrode 104 and a lead 106 connecting electrode 104 to the control unit 102. The lead 106 includes a proximal end 114 that is coupled to the control unit 102 via a connector 115 and a distal end 116 at which the electrode 104 is located. Additional leads 106 or sensors 108 may be coupled to the control unit 102 at a suitable interface, such as interface 118.

The electrode 104 can be anchored to a pelvic floor muscle of the patient (e.g., the external urinary or anal sphincter), by means of a fixation element 120, such as a helix, spiral hook, polypropylene mesh, or other anchor known in the art, as shown in the magnified schematic illustration of the distal end 116 of the lead 106 provided in FIG. 2. The helix or spiral hook 120 can be embedded within the external urinary sphincter to anchor the lead 106 thereto. In one embodiment, the fixation element 120 operates to provide electrical contact between the muscle and one or more stimulation electrodes 104A and 104B disposed on a silicone casing 122 of the lead 106.

In one embodiment, the electrodes, generally referred to as 104, are approximately 3 millimeters in length, but can be much longer, such as less than about 80 millimeters in length, for example. The electrodes 104 are typically separated by approximately 3 millimeters along the length of the lead 106. In the same between the electrodes 104A and 104B a tip 124 of an EMG wire 126 may protrude approximately 100 microns through the casing 124, for those applications in which EMG sensing is desirable. Typically, the diameter of the wire 126 is approximately 50 microns, and the diameter of the casing 124 is approximately 1.5 millimeters.

As with the device 100 illustrated in FIG. 1, one embodiment of the device 100 illustrated in FIG. 2 comprises circuitry for applying electrical stimulation waveforms to the muscular tissue, in which the fixation element 120 is embedded and/or for sensing electrical signals received by the electrodes 104, in accordance with conventional implantable electronic stimulator devices known in the art.

Embodiments of the invention are directed to a method of installing the distal end 116 of the stimulation lead 106 into a pelvic floor muscular structure of a patient that is deep to, or below the pubic symphysis. in one embodiment, the pelvic floor muscular structure being targeted by the distal end 116 of the stimulation lead 106 is the external urinary sphincter of the patient, as described in detail below. Other exemplary pelvic floor muscular structures that may be implanted with the distal end of the stimulation lead using embodiments of the method include Puborectalis, Pubococcygeus, and Iliococcygeus (individual elements of the Lavator ani muscular complex). It is understood that while embodiments of the method will be described with regard to the implantation of the distal end 116 of the stimulation lead 106 into the external urinary sphincter of the patient, many of the embodiments are applicable to methods of implanting the distal end 116 in one or more of the other exemplary pelvic floor muscular structures mentioned above.

Figure 3:
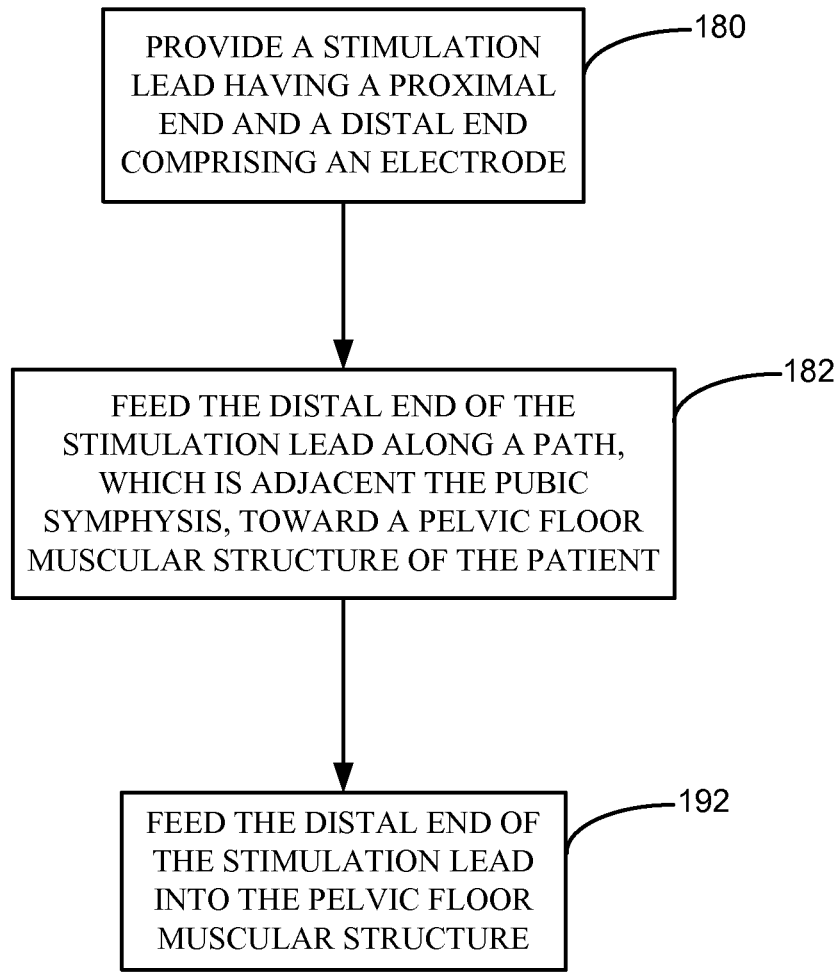
FIG. 3 is a flowchart illustrating steps of a method in accordance with embodiments of the invention.
Figure 4:
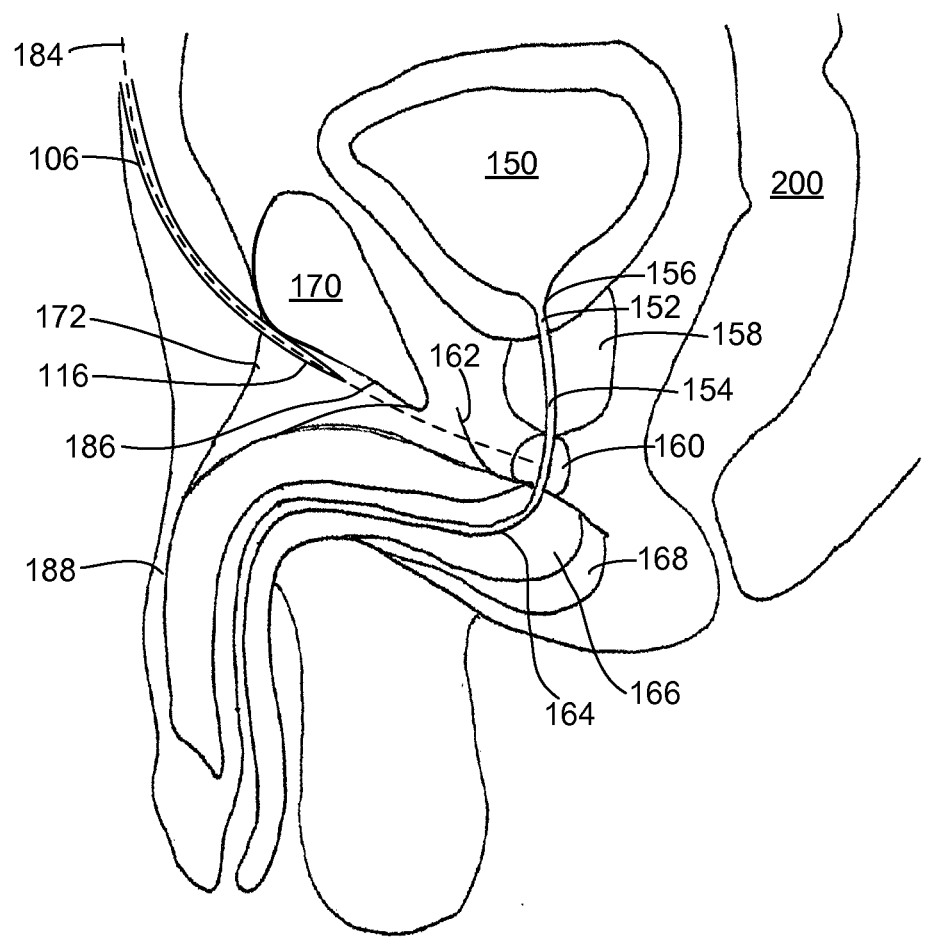
FIGS. 4 and 5 are simplified cross-sectional views of a male patient illustrating steps of the method of FIG. 3 in accordance with embodiments of the invention.
Figure 5:
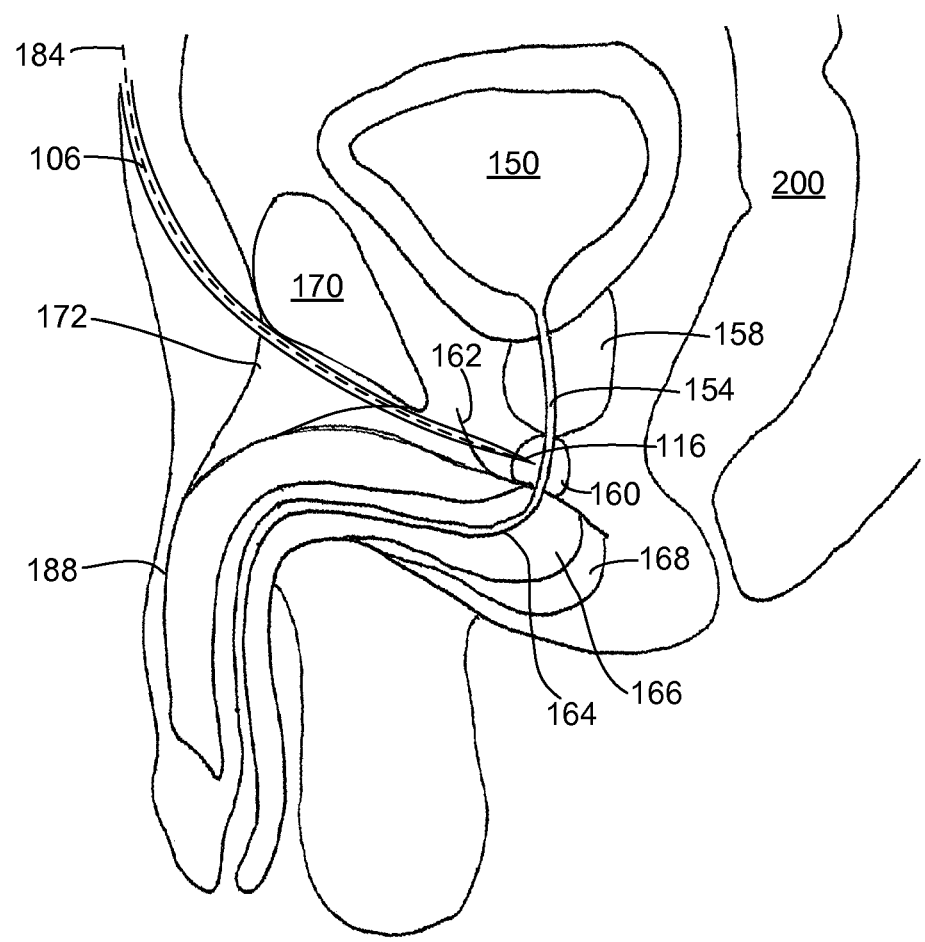

FIG. 3 is a flowchart illustrating steps of the method, embodiments of which will initially be discussed with reference to FIGS. 4 and 5, which are cross-sectional views of the pelvic region of a male patient. FIGS. 4 and 5 illustrate certain pelvic anatomy including the bladder 150 that connects to a proximal end 152 of the urethra 154, at the bladder neck 156. The urethra 154 extends distally from the bladder 150 through the prostate 158 and the external urinary sphincter 160 and below the prostate 158 through the perineal membrane 162. The portion of the urethra 154 located distally relative to the perineal membrane 162 is referred to as the "bulbar urethra" 164. Tissue below the perineal membrane 162 and the bulbar urethra 164 includes the corpus spongiosum 166 and the bulbospongiosus muscle 168. Also illustrated is the pubic symphysis 170 and the suspensory ligament 172 located adjacent the notch in the posterior edge of the pubic symphysis 170. While the drawings are of a male patient and some of the method steps are only applicable to male patients, it is understood that embodiments of the present invention may be applied to female patients.

At step 180 of the method, a stimulation lead, such as the lead 106 (FIGS. 1 and 2) in accordance with one or more of the embodiments described above, is provided. The stimulation lead 106 has proximal end 114 and a distal end 116. In one embodiment, the distal end 116 comprises one or more electrodes 104, as illustrated in FIG. 2.

At step 182, after the patient has been properly prepared for surgery, the distal end 116 of the stimulation lead 106 is fed along a path 184, which is adjacent the pubic symphysis 170, toward the pelvic floor muscular structure of the patient, such as the depicted external urinary sphincter 160, as illustrated in FIG. 4. In one embodiment, the path 184 is positioned between the ventral face 186 of the pubic symphysis 170 and the penis 188. The path 184 preferably avoids contacting the vessels and nerves across the top of the penis 188 during the feeding step 182 and subsequent steps of the method. A conventional introducer can bee used to feed the distal end 116 of the stimulation lead 106 along the path 184.

Figure 6:
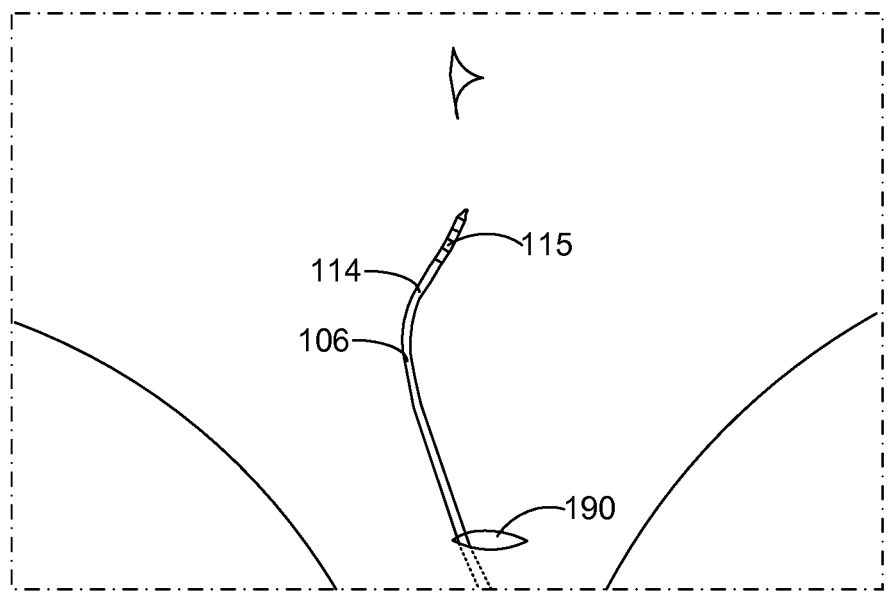
FIG. 6 is a partial frontal view of a male patient.

In one embodiment, an incision 190 is initially made in the patient adjacent the notch in the posterior edge of the pubic symphysis 170 through which the distal end 116 of the stimulation lead 106 is fed into the patient along the path 184 in step 182, as illustrated in the frontal view of the patient provided in FIG. 6. In one embodiment, the incision is approximately 1.5-2 cm lateral to the notch in the pubic symphysis 170. The notch and the adjacent suspensory ligament 172 can be located, for example, by placing the penis 188 of the male patient on a stretch and palpating for the notch in the posterior edge of the pubic symphysis 170.

At step 192 of the method, the distal end 116 of the stimulation lead 106 is fed along the path 184 and into the desired pelvic floor muscular structure of the patient, such as the depicted external urinary sphincter 160, at an insertion point 194 to place the one or more electrodes 104 in contact with the external urinary sphincter 160 or another desired pelvic floor muscular structure, as illustrated in FIG. 5.

Figure 7:
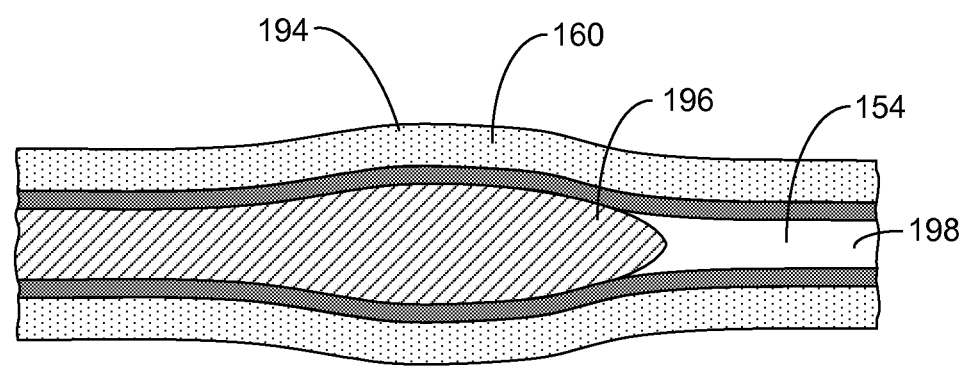
FIG. 7 is a simplified cross-sectional view of the external urinary sphincter and urethra of a patient with a probe inserted in the urethra.

Many techniques can be used to approximate the location of the external urinary sphincter 160 and the urethra 154 of the patient to assist in the feeding step 192. In one embodiment, a catheter or probe 196 is fed into the urethra 154 of the patient and positioned approximate the desired insertion point 194 of the external urinary sphincter 160, as illustrated in FIG. 7. FIG. 7 is a simplified cross-sectional view of the external urinary sphincter 160 and urethra 154 of the patient. The bladder side of the probe 196 is indicated at 198. In one embodiment, the probe 194 comprises an ultrasound probe, which can be used to approximate the location of the distal end 116 of the stimulation lead 106 relative to the probe 196 and, thus, determine the location of the distal end 116 of the stimulation lead 106 relative to the urethra 154 and external urinary sphincter 160 of the patient.

In accordance with another embodiment, the surgeon palpates for the probe 196 through the rectum 200 (FIGS. 4 and 5) to feel the location of the probe 196 within the urethra 154 adjacent to the desired insertion point 194 of the external urinary sphincter 160.

In yet another embodiment, the surgeon may palpate for the prostate 158 of the patient, from which the location of the external urinary sphincter 160 can be approximated.

In one embodiment, the path 184 passes through the perineal membrane 162 of the patient. Thus, during the feeding step 192, the distal end 116 of the stimulation lead 106, or an introducer used to feed the stimulation lead 106, encounters the perineal membrane 162 and an increase in resistance to the feeding of the distal end 116 can be sensed by the surgeon. This increase in resistance is followed by a decrease in resistance upon piercing the perineal membrane 162. Accordingly, the sensed decrease in resistance indicates that the distal end 116 of the stimulation lead 106 is positioned slightly beyond the perineal membrane 162. In one embodiment, upon sensing the piercing of the perennial membrane 162, the surgeon feeds the distal end 116 of the stimulation lead 106 approximately 1 cm to place the distal end 116 and the one or more electrodes 104 within the external urinary sphincter 160.

Figure 8:
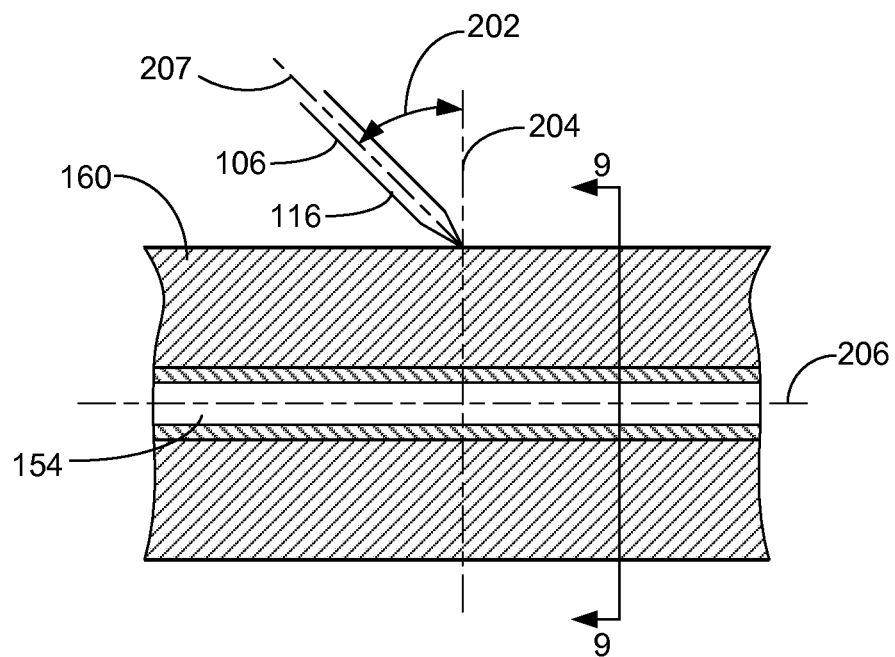
FIG. 8 is a simplified cross-sectional view of the external urinary sphincter and the urethra of a patient illustrating the insertion of a distal end of a stimulation lead in accordance with embodiments of the invention.

In one embodiment, the feeding step 192 comprises feeding the distal end 116 of the stimulation lead 106 into the external urinary sphincter 160 at the insertion point 194 at an angle 202 that is oblique to a plane 204 extending perpendicular to a central axis 206 of the urethra 154 and through the insertion point 194, as illustrated in FIG. 8, which is a simplified cross-sectional view of the external urinary sphincter 160 and the urethra 154 of the patient. The central axis 206 is defined as the approximate center of the urethra 154 aligned parallel to the general flow of fluid through the urethra 154. The angle 202 is measured from the plane 204 to a central axis 207 of the stimulation lead 106. In one embodiment, the angle 202 is in the range of 0-45 degrees.

Figure 9:
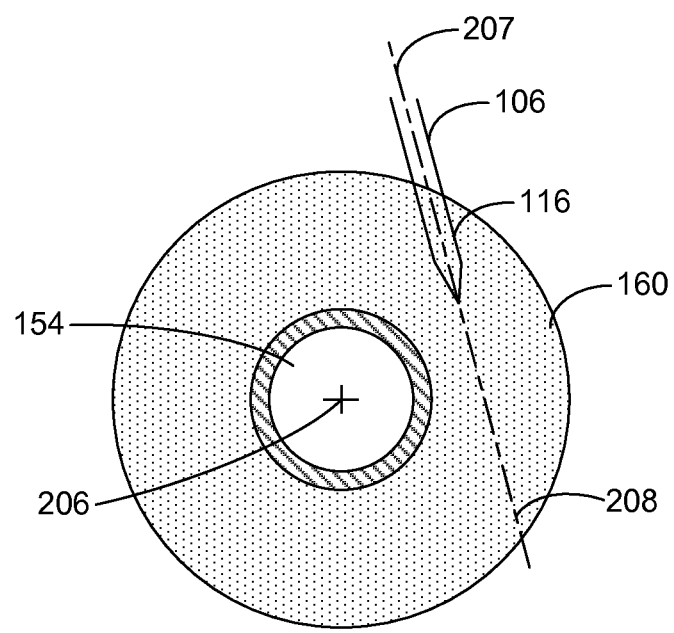
FIG. 9 is a simplified cross-sectional view of the external urinary sphincter and the urethra of a patient taken generally along line 9-9 of FIG. 8.

In accordance with another embodiment, the feeding step 192 comprises feeding the distal end 116 of the stimulation lead 106 into the external urinary sphincter 160 along a path 208 that does not intersect the urethra 154, as illustrated in FIG. 9, which is a simplified cross-sectional view of the external urinary sphincter 160 and the urethra 154 of the patient taken generally along line 9-9 of FIG. 8. This ensures that the distal end 116 of the stimulation lead 106 does not pierce the urethra 154.

In one embodiment, a helical coil, a suture, or other conventional anchor or fixation element 120 (FIG. 2) may be attached to the distal end 116 of the stimulation lead 106 and embedded in the external urinary sphincter 160 or other desired pelvic floor muscular structure of the patient. The anchor 120 operates to resist relative movement between the distal end 116 of the lead 106 and the sphincter tissue.

After the feeding step 192 is completed, the one or more electrodes 104 at the distal end 116 of the lead 106 can be used to sense signals conducted through the pelvic floor muscular structure and/or apply electrical signals to the pelvic floor muscular structure when the proximal end 114 of the stimulation lead 106 is connected to the control unit 102. In one embodiment, after the feeding step 192 is completed, the one or more electrodes 104 can be used to sense signals conducted through the external urinary sphincter 130 and/or apply electrical signals to the external urinary sphincter 130, when the proximal end 114 of the stimulation lead 106 is connected to the control unit 102.

Additional embodiments of the invention are directed to connecting the control unit 102 to the lead 106 and implanting the control unit 102 in the patient. In one embodiment, the proximal end 114 of the stimulation lead 106 is connected to the control unit 102. In one embodiment, the control unit 102 generates electrical signals that are applied to the external urinary sphincter 160 through the one or more electrodes 104 at the distal end 116 of the stimulation lead 106 that are embedded in the pelvic floor muscular structure to treat pelvic pain, urinary incontinence and/or another pelvic condition of the patient. In one embodiment, the control unit 102 receives signals from the one ore more electrodes 104 embedded in the pelvic floor muscular structure, such as the external urinary sphincter 160, or from a sensor 108 (FIG. 1), and applies the electrical signals to the pelvic floor muscular structure through one or more of the electrodes 104 of the stimulation lead 106 responsive to the received signals.

Figure 10:
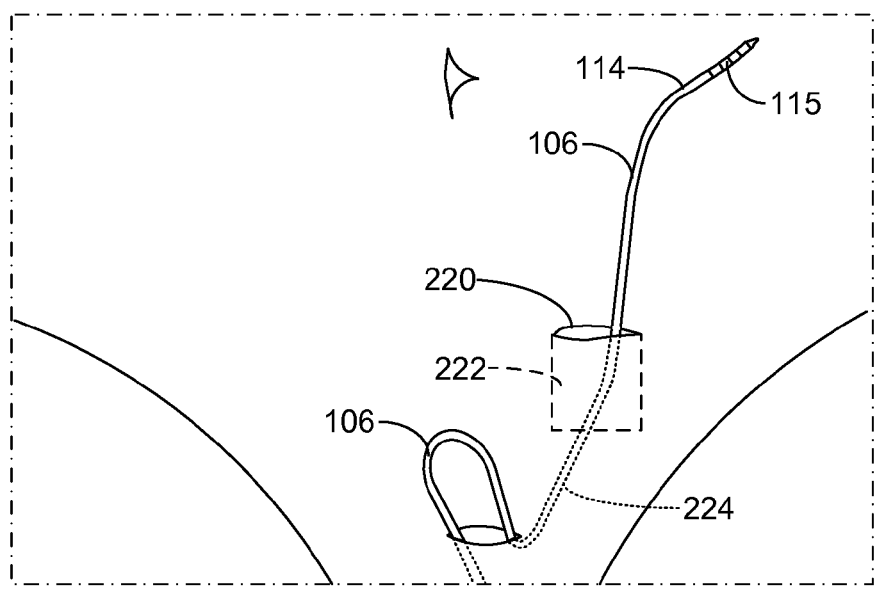
FIGS. 10-12 Illustrate various steps of a method of implanting an electrode of an electronic stimulator device in an external urinary sphincter of a male patient, in accordance with embodiments of the invention.
Figure 11:
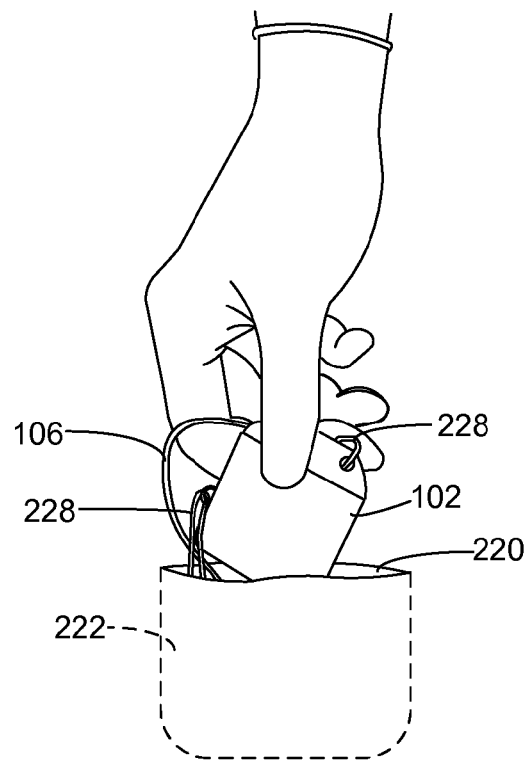

Additional embodiments of the method will be discussed with reference to FIGS. 10-12, which Illustrate various steps of a method of implanting an electrode of an electronic stimulator device in a pelvic floor muscular structure of the patient, such as the external urinary or anal sphincter, in accordance with embodiments of the invention. In one embodiment, an incision 220 is formed in the patient, as shown in the frontal view of the patient provided in FIG. 10. In one embodiment, the incision 220 is formed in the abdomen of the patient. In one embodiment, the incision 220 comprises a 2-3 centimeter long, horizontal skin incision that is approximately 6 centimeters lateral to and 4 centimeters cephalad to the pubic symphysis bone 170 of the patient. In one embodiment, the incision 220 is formed in the subcutaneous tissue adjacent to the fascia of the abdomen of the patient using blunt dissection to form an abdominal pocket 222. In one embodiment, the abdominal pocket 222 is sized to accommodate a control unit 102 of an implantable electronic stimulator device, such as one of the exemplary control units 102 described above. Thus, for example, the abdominal pocket 222 may comprise a depth of approximately 4 centimeters in order to accommodate the control unit 102. An antibiotic soaked pad may be placed in the abdominal pocket 222.

In one embodiment, a subcutaneous tunnel 224 is formed between the incision 190 and the incision 220 using, for example, a suitable introducer, such as those described in U.S. patent application Ser. No. 11/961,615 filed Dec. 20, 2007, which is incorporated herein by reference in its entirety. In one embodiment, the proximal end 114 of the stimulation lead 106 is then fed through the tunnel 224 and out the incision 220, as illustrated in FIG. 10, which is a partial frontal view of the patient. The feeding of the proximal end 114 of the stimulation lead 106 through the tunnel 224 can be accomplished by pushing the proximal end 114 through a tube (not shown) installed in the tunnel 224, pulling the proximal end 114 through the tunnel 224 or other conventional technique. Additionally, it is understood that the feeding of the stimulation lead 106 through the tunnel 224 may be accomplished prior to the feeding of the distal end 116 of the stimulation lead 106 into the external urinary sphincter of the patient. In such a case, the distal end 116 of the stimulation lead 106 may be fed (i.e., pulled or pushed) through the tunnel 224 from the incision 220 and out the incision 190. Once the stimulation lead 106 is fed through the tunnel 224, slack in the stimulation lead is eliminated and the incision 190 can be closed.

In one embodiment, with the stimulation lead 106 extending from the external urinary sphincter 160 of the patient, through the tunnel 224 and out the incision 220, the connecting portion 115 at the proximal end 114 is installed in a corresponding socket 226 of the control unit 102 (FIG. 2), to complete the assembly of the electrical stimulation device 100. In one embodiment, a seal is formed between the socket 226 and the connector 115 using an o-ring or other suitable component, to prevent fluids from entering the socket 226.

The device 100 is preferably tested to ensure that it is working properly including, for example, generating the desired electrical waveforms and applying the electrical waveforms or signals to the external urinary sphincter 160 through the one or more electrodes 104. If the device 100 is operating properly, the lead 106 can be tucked into the abdominal pocket 222 and sutures 228 are looped through suture holes 230 (FIG. 2) and used to secure the control unit 102 to the fascia within the pocket, as illustrated in FIG. 11. In one embodiment, the control unit 102 is located 4 centimeters or less from the surface of the skin in the subcutaneous tissue to allow the unit 102 to receive programming signals. Once the control unit 102 is secured within the abdominal pocket 222, the incision 220 is sealed to complete the implantation of the device 100 in the patient.

It may be desirable to test the device 100 for several days to three weeks to determine whether the device 100 is working as desired and/or whether the patient is a suitable candidate for the device 100. In accordance with one embodiment of the method, the control unit 102 is not connected to the connector 115 of the lead 106 following the feeding of the proximal end 114 through the tunnel 224 and out the incision 220, and the control unit is not initially installed in the abdominal pocket 222.

Figure 12:
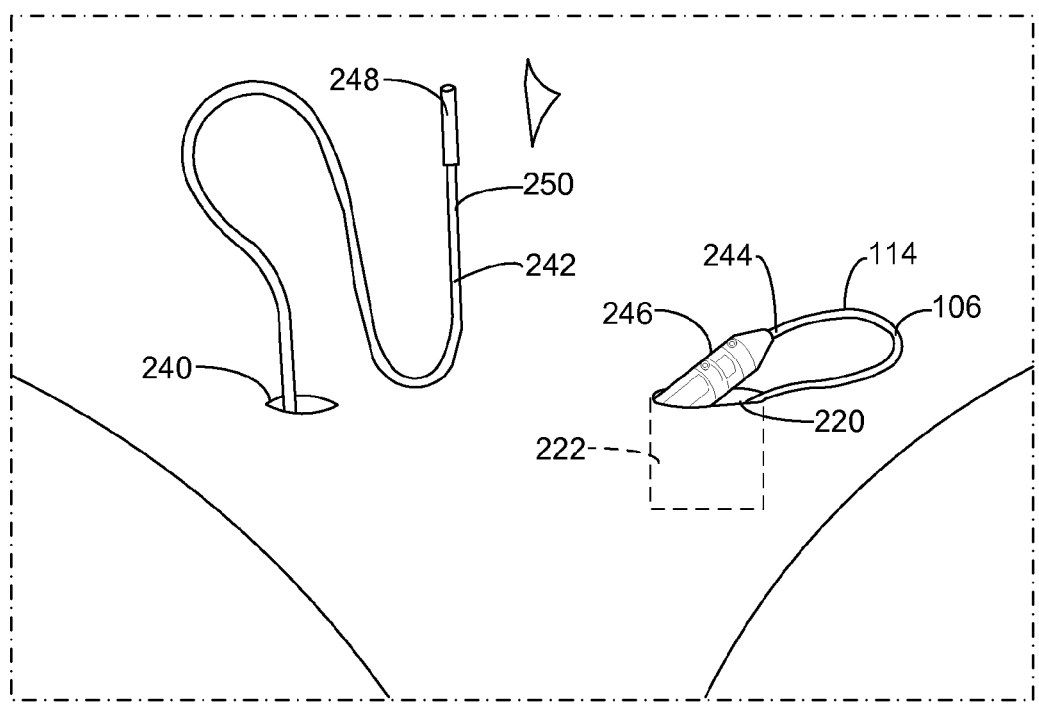

In one embodiment, an incision 240, such as a horizontal incision approximately 1 centimeter long, is made on the contralateral side of the patient's abdomen, as shown in FIG. 12. In one embodiment, the incision 240 is approximately 15 centimeters from the initial abdomen incision 220. In one embodiment, a subcutaneous tunnel is formed between the incision 220 and the incision 240, in accordance with conventional methods. An extension lead 242 is fed through the tunnel such that the ends of the lead 242 extend outside the incisions 240 and 220. In one embodiment, a distal 244 end of the extension lead 242 is attached to the proximal end 114 of the stimulation lead 106, as illustrated in FIG. 12. In one embodiment, the distal end 244 of the extension lead 242 includes a socket 246 to which the connector 115 at the proximal end 114 of the lead 106 is attached. In one embodiment, the socket 246 receives the connector 115 and set screws are used to secure the connection. A seal is preferably formed between the socket 246 and the connector 115 using an o-ring or other suitable component to prevent fluids from entering the socket 246 in accordance with conventional methods. The socket 246 of the extension lead 242 and the proximal end 114 of the lead 106 are packed into the abdominal pocket 222, as illustrated in FIG. 12. The incision 220 is then closed over the lead extension socket 246 in two layers.

A connector 248 at the proximal end 250 of the extension lead 242 is then installed in the socket 226 of the control unit 102 or other testing unit that is external to the patient. The connection of the control unit 102 to the extension lead 242 via connector 248, and the extension lead 242 to the lead 106 via the installation of the connector 115 in the socket 246, allows the control unit 102 or testing device to send electrical signals to, and/or receive electrical signals from, the one or more electrodes 104 embedded in the pelvic floor muscular structure of the patient. Testing of the device 100 can then commence. The control unit can be worn on a belt outside of the body of the patient, if desired.

If the testing of the device 100 and the installed lead 106 is successful, the incision 220 can be reopened to expose the socket 246 and the connector 115. The connector 115 is disconnected from the socket 246 and the extension lead 242 is pulled through the incision 240. The connector 115 can then be installed directly in the socket 226 of the control unit and installed in the abdominal pocket of the patient as described above to complete the implantation of the device 100 in the patient.

Although the present invention has been described with reference to preferred embodiments, workers skilled in the art will recognize that changes may be made in form and detail without departing from the spirit and scope of the invention.

What is claimed is:

1. A method comprising:
providing a stimulation lead having a proximal end and a distal end comprising an electrode;
feeding the distal end of the stimulation lead along a path, which is adjacent the pubic symphysis of a patient, toward a pelvic floor muscular structure of the patient; and
feeding the distal end of the stimulation lead into the pelvic floor muscular structure.

2. The method of claim 1, wherein the method further comprises:
making a first incision in the patient adjacent the notch in the posterior edge of the pubic symphysis; and
feeding the distal end of the stimulation lead from outside the patient's body through the first incision and toward the ventral face of the pubic symphysis.

3. The method of claim 2, wherein feeding the distal end of the stimulation lead into the pelvic floor muscular structure comprises:
feeding the distal end of the stimulation lead toward the pelvic floor muscular structure;
piercing the perineal membrane; and feeding the distal end of the stimulation lead into the pelvic floor muscular structure.

4. The method of claim 3, wherein the pelvic floor muscular structure comprises at least one of the group consisting of the external urinary sphincter muscle, the external anal sphincter muscle, the levator ani muscle, the puborectalis sling muscle and prostate tissue of the patient.

5. The method of claim 4, wherein feeding the distal end of the stimulation lead into the pelvic floor muscular structure comprises feeding the distal end into an insertion point of the external urinary sphincter at an angle that is approximately 0-45 degrees to a plane extending perpendicular to a central axis of the urethra and through the insertion point.

6. The method of claim 4, wherein feeding the distal end of the stimulation lead into the pelvic floor muscular structure comprises feeding the distal end into the external urinary sphincter along a line that does not intersect the urethra.

7. The method of claim 4, wherein feeding the distal end of the stimulation lead into the pelvic floor muscular structure comprises:
feeding a probe into the urethra of the patient and positioning the probe proximate a desired insertion point of the external urinary sphincter; and
feeding the distal end of the stimulation lead into the external urinary sphincter proximate the desired insertion point and the probe.

8. The method of claim 1, further comprising:
connecting the proximal end of the stimulation lead to a control unit;
generating electrical signals using the control unit; and
applying the electrical signals to the pelvic floor muscular structure through the electrode.

9. The method of claim 4, further comprising:
making a second incision in the abdomen of the patient, wherein the second incision is displaced from the first incision; and
feeding the proximal end of the lead through a subcutaneous tunnel between the first incision and second incisions, and out the second incision.

10. The method of claim 9, further comprising:
forming a subcutaneous pocket at the second incision;
connecting the proximal end of the stimulation lead to a control unit; and
implanting the control unit in the subcutaneous pocket.

11. The method of claim 9, further comprising:
making a third incision in the abdomen of the patient, wherein the third incision is displaced from the first and second incisions; and
coupling a first end of an extension lead to the proximal end of the stimulation lead; and
feeding a second end of the extension lead through a subcutaneous tunnel between the second incision and the third incision, and out the third incision.

12. The method of claim 11, further comprising:
connecting the second end of the stimulation lead to a control unit;
generating electrical signals using the control unit; and
applying the electrical signals to the external urinary sphincter through the electrode.

13. The method of claim 12, further comprising:
disconnecting the second end of the extension lead from the control unit;
disconnecting the first end of the extension lead from the proximal end of the stimulation lead;

removing the extension lead from the subcutaneous tunnel;
coupling the proximal end of the stimulation lead to the control unit;
generating electrical signals using the control unit; and
delivering the electrical signals to the external urinary sphincter through the stimulation lead and the electrode.

14. The method of claim 1, wherein:
the patient is a male patient; and
feeding the distal end of the stimulation lead along a path comprises feeding the distal end of the stimulation lead between the ventral face of the pubic symphysis and the penis of the patient.

15. A method comprising:
providing a stimulation lead having a proximal end and a distal end comprising an electrode;
making a first incision in the patient;
feeding the distal end of the stimulation lead from outside the patient's body through the first incision and alongside the ventral face of the pubic symphysis and toward the external urinary sphincter of the patient; and
feeding the distal end of the stimulation lead into an insertion point of the external urinary sphincter at an angle that is approximately 0-45 degrees to a plane extending perpendicular to a central axis of the urethra and through the insertion point.

16. The method of claim 15, wherein feeding the distal end of the stimulation lead into the external urinary sphincter comprises:
feeding the distal end of the stimulation lead toward the urinary sphincter;
piercing the perineal membrane; and
feeding the distal end of the stimulation lead into the external urinary sphincter.

17. The method of claim 15, wherein feeding the distal end of the stimulation lead into an insertion point of the external urinary sphincter comprises:
feeding a probe into the urethra of the patient and positioning the probe proximate the insertion point of the external urinary sphincter; and
feeding the distal end of the stimulation lead into the external urinary sphincter into the insertion point proximate the probe.

18. The method of claim 15, further comprising:
connecting the proximal end of the stimulation lead to a control unit;
generating electrical signals using the control unit; and
applying the electrical signals to the external urinary sphincter through the electrode.

19. The method of claim 18, further comprising:
making a second incision in the abdomen of the patient, wherein the second incision is displaced from the first incision; and
feeding the proximal end of the lead through a subcutaneous tunnel between the first incision and second incisions, and out the second incision.

20. The method of claim 19, further comprising:
forming a subcutaneous pocket at the second incision;
connecting the proximal end of the stimulation lead to a control unit; and
implanting the control unit in the subcutaneous pocket.

* * * * *